(12) United States Patent
Lee et al.

(10) Patent No.: US 12,370,274 B2
(45) Date of Patent: Jul. 29, 2025

(54) APPARATUS FOR GENERATING AND TRANSPORTING SPECTRAL LINE RADIATION

(71) Applicant: Ion Medical Inc., Seongnam-si (KR)

(72) Inventors: Keunho Lee, Seoul (KR); Postel Olivier, Colorado Springs, CO (US)

(73) Assignee: Ion Medical Inc., Seongnam-si (KR)

( * ) Notice: Subject to any disclaimer, the term of this patent is extended or adjusted under 35 U.S.C. 154(b) by 960 days.

(21) Appl. No.: 17/500,608

(22) Filed: Oct. 13, 2021

(65) Prior Publication Data

US 2022/0165447 A1 May 26, 2022

(30) Foreign Application Priority Data

Nov. 26, 2020 (KR) .......................... 10-2020-0161238

(51) Int. Cl.
*A61L 2/00* (2006.01)

(52) U.S. Cl.
CPC .................................. *A61L 2/0029* (2013.01)

(58) Field of Classification Search
CPC ...................................................... A61L 2/0029
See application file for complete search history.

(56) References Cited

U.S. PATENT DOCUMENTS

| 2008/0196582 A1* | 8/2008 | Tjeenk Willink | .... B01D 53/007 95/57 |
| 2012/0156094 A1* | 6/2012 | Gordon | ..................... A61L 2/10 250/492.1 |
| 2020/0300769 A1* | 9/2020 | Dominick | ................ H05H 1/52 |

FOREIGN PATENT DOCUMENTS

| KR | 20180003955 A | 1/2018 |
| KR | 102075467 B1 | 2/2020 |
| KR | 20200101055 A | 8/2020 |
| KR | 20210109933 A | 9/2021 |

* cited by examiner

*Primary Examiner* — Nicole M Ippolito
(74) *Attorney, Agent, or Firm* — NKL LAW; Jae Youn Kim

(57) ABSTRACT

Disclosed is an apparatus for generating and transporting spectral line radiation which may transmit radiation generated from a radiation source accurately to a target. The apparatus includes a radiation source configured to emit atomic, ionic or molecular spectral line radiation, a transmission nozzle configured to transmit the spectral line radiation emitted by the radiation source to the target, and a gas supply channel configured to supply gas in the same environment as the spectral line radiation emitted by the radiation source to an environment around the target.

10 Claims, 7 Drawing Sheets

APPARATUS FOR GENERATING AND TRANSPORTING SPECTRAL LINE RADIATION

CROSS-REFERENCE TO RELATED APPLICATION

This application claims priority to and the benefit of Korean Patent of Application No. 10-2020-0161238, filed on Nov. 26, 2020, the disclosure of which is incorporated herein by reference in its entirety.

BACKGROUND OF THE INVENTION

Field of the Invention

The present invention relates to an apparatus for generating and transporting spectral line radiation, and more particularly, to an apparatus for generating and transporting spectral line radiation which may transmit radiation generated from a radiation source accurately to a target.

Description of the Related Art

In general, radiation is a beam made by particles emitted due to radioactive decay, and is being used in various fields, such as medical technologies, semiconductor manufacture, etc.

Particularly, radiation having a narrow spectrum which may be generated from various sources, such as gas discharge plasma or a laser, is effectively transmitted to a target to be exposed due to self absorption and re-emission of radiation (known as radiation trapping), and in radiation trapping, radiation is re-distributed directionally and is thus effectively transmitted to a region above or behind the target or into cracks, holes or via holes formed in the target when the radiation is buried in gas of the same type as gas used in generation of line radiation or when another source radiation exists.

There are various technologies using such radiation and, for example, Patent Documents 1 to 4 disclose these technologies.

Patent Document 1 discloses a device for generating a flattened X-ray radiation field provided with a plurality of electron accelerators used for generating high-energy electron beam currents, and a common target unit including a vacuum target chamber, a target and a plurality, of input connection devices, the plurality of electron accelerators being connected with the plurality of input connection devices, respectively, the plurality of input connection devices being mounted on one side of the vacuum target chamber, the target being mounted on the other side of the vacuum target chamber opposite the plurality of input connection devices, and the axes of the plurality of input connection devices intersecting at one point in such a manner that a preset included angle is formed between every two axes, so as to flatten an X-ray radiation field generated by the electron accelerators.

Patent Document 2 discloses a radiographic testing apparatus for structures including a target unit configured to support an upper target and a lower target at one side of an object to be tested, a radiation unit provided with a distance meter and a radiation source on a main carriage traveling above the other side of the object to be tested, a detection unit provided with a distance meter and a detector on a sub-carriage traveling below the other side of the object to be tested, and a control unit configured to control the target unit, the radiation unit and the detection unit through a set algorithm.

Patent Document 3 discloses a target device including a housing provided with a vacuum chamber formed therein, an inner case configured to have a cylindrical shape, installed inside the housing and provided with an electron beam inlet formed in the front surface of the inner case so that an electron beam is incident upon the housing, a cover plate fixedly installed on the housing so as to cover an open one end of the housing, a drive unit provided with a rotating shaft installed to pass though the cover plate and the inner case and a motor configured to rotate the rotating shaft, and a radiation generating target coupled to the rotating shaft so as to be rotated in one direction and configured to collide with the incident electron beam so as to generate radiation having different energies, a radiation hole being formed at the position of the cover plate overlapping the electron beam inlet, and the radiation generated by the radiation generating target through the radiation hole passing through the target device.

Patent Document 4 discloses an irradiation target handling device having an isotope production cable assembly, including a drive cable constructed to be compatible with the drive mechanism requirements for an existing nuclear reactor drive mechanism for cable drive systems used to insert and withdraw sensors within nuclear reactor cores, having a spirally wound, self-powered radiation detector wrapped around an axial length of the drive cable proximate one end designed to be inserted into a flux thimble in a core of a nuclear reactor with a length of the self-powered radiation detector sufficient to provide a preselected signal output with a minimal axial length from end to end of the spiral, so the self-powered radiation detector provides an output indicative of reactor flux at the self-powered radiation detector position in a reactor core to enable an axial position of a target material supported by and proximate the one end of the drive cable to be optimized, one of a female end or male end of a quick disconnect coupling attached to the one end of the drive cable, and a target holder element cable assembly having another of the female end or the male end of the quick disconnect coupling at one end of the target holder element cable assembly, configured to attach to and detach from the one of the female or male end, the target holder element cable assembly having a target material support compartment configured to securely hold the target material as the drive cable is inserted and withdrawn through the flux thimble.

The above-described various technologies using radiation have been developed, but these technologies have a limit in transmitting radiation accurately to a target.

RELATED ART DOCUMENT

Patent Document (Patent Document 0001) Korean Patent Unexamined Publication No. 10-2016-0083847
(Patent Document 0002) Korean Patent Unexamined Publication No. 10-2020-0025188 (Patent Document 0003) Korean Patent Registration No. 10-2075467
(Patent Document 0004) Korean Patent Unexamined Publication No. 10-2019-0019213

SUMMARY OF THE INVENTION

Therefore, the present invention has been made in view of the above problems, and it is an object of the present invention to provide an apparatus for generating and transporting spectral line radiation which may transmit radiation generated from a radiation source accurately to a target.

In accordance with the present invention, the above and other objects can be accomplished by the provision of an apparatus for generating and transporting spectral line radiation so as to apply the spectral line radiation to a target, the apparatus including a radiation source configured to emit atomic, ionic or molecular spectral line radiation, a transmission nozzle configured to transmit the spectral line radiation emitted by the radiation source to the target, and a gas supply channel configured to supply gas in the same environment as the spectral line radiation emitted by the radiation source to an environment around the target.

The apparatus may further include a transfer conduit configured to transmit the spectral line radiation emitted by the radiation source to the transmission nozzle.

The radiation source may be any one of a plasma device, a laser device and a light emitting diode.

A transmissive window may be further installed in at least one of the radiation source and the transfer conduit.

A reflective plate may be further installed on an inner wall of the radiation source.

An inner wall of the transfer conduit may have high reflection characteristics at wavelengths of the spectral line radiation emitted by the radiation source.

The transmission nozzle may be one of an enclosure, an orifice and a cup.

An indicator may be further provided at one side of the apparatus.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
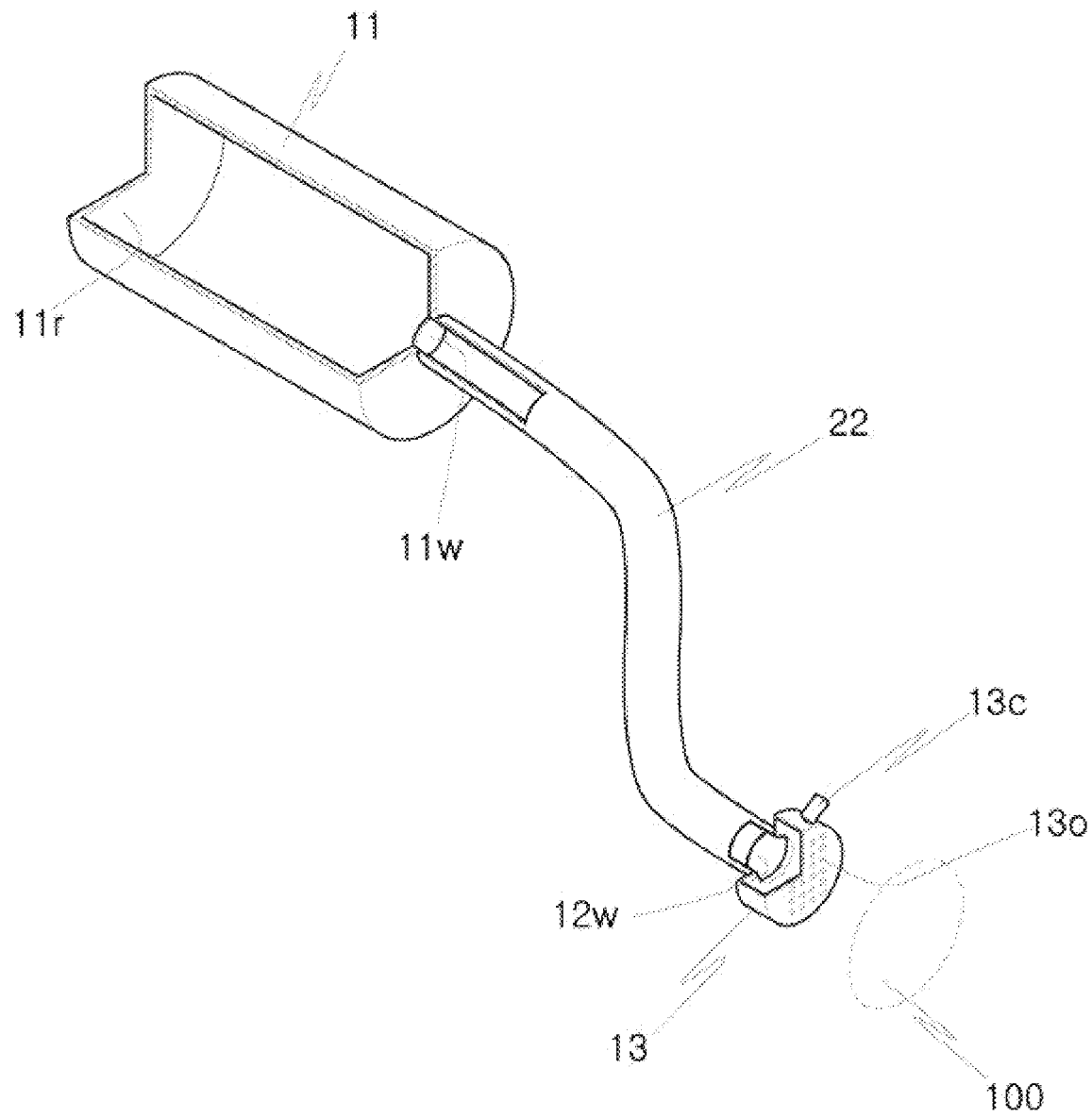
FIG. 1 is a perspective view of an apparatus for generating and transporting spectral line radiation according to one embodiment of the present invention.

Hereinafter, reference will be made in detail to various embodiments of the present invention, examples of which are illustrated in the accompanying drawings and described below. While the invention will be described in conjunction with exemplary embodiments, it will be understood that the present description is not intended to limit the invention to the exemplary embodiments. On the contrary, the invention is intended to cover not only the exemplary embodiments, but also various alternatives, modifications, equivalents and other embodiments, which may be included within the spirit and scope of the invention as defined by the appended claims.

In the drawings, the same or similar elements are denoted by the same reference numerals even though they are depicted in different drawings. In the following description of the present invention, a detailed description of known functions and configurations incorporated herein will be omitted when it may make the subject matter of the present invention rather unclear.

The present invention is configured so as to emit radiation emitted by a radiation source accurately to a desired area.

An apparatus for generating and transporting spectral line radiation according to the present invention is an apparatus which radiates light to a target 100, as shown in FIGS. 1 to 6, and includes a radiation source 11, 21, 31, 41, 51 or 61 configured to emit atomic, ionic or molecular spectral line radiation, a transmission nozzle 13, 23, 33, 43, 53 or 63 configured to transmit the radiation emitted by the radiation source 11, 21, 31, 41, 51 or 61 to a target 100, and a gas supply channel 13c, 23c, 32c, 43c, 53c or 62c configured to supply gas of the same environment as gas used to generate the spectral line radiation emitted by the radiation source 11, 21, 31, 41, 51 or 61 to the environment around the target.

The radiation source 11, 21, 31, 41, 51 or 61 has a tubular form, and a transfer conduit 12, 22, 32, 42, 52 or 62 configured to transmit the radiation emitted by the radiation source 11, 21, 31, 41, 51 or 61 to the transmission nozzle 13, 23, 33, 43, 53 or 63 is connected to the radiation source 11, 21, 31, 41, 51 or 61.

The radiation source 11, 21, 31, 41, 51 or 61 may be manufactured in various types and, for example, may be any one of a plasma device, a laser device and a light emitting diode.

When the radiation source 11, 21, 31, 41, 51 or 61 is a plasma device, discharge is generated by a normal electric field, an oscillating electric field or a combination of an oscillating electric field and an applied magnetic field, and in this case, a plasma density may be improved through helicon, electron cyclotron or ion cyclotron resonance.

Transmissive windows 11w, 31w, 41w or 61w and/or 12w, 22w or 42w may be installed in at least one of the radiation source 11, 21, 31, 41, 51 or 61 and the transfer conduit 12, 22, 32, 42, 52 or 62.

Figure 2:
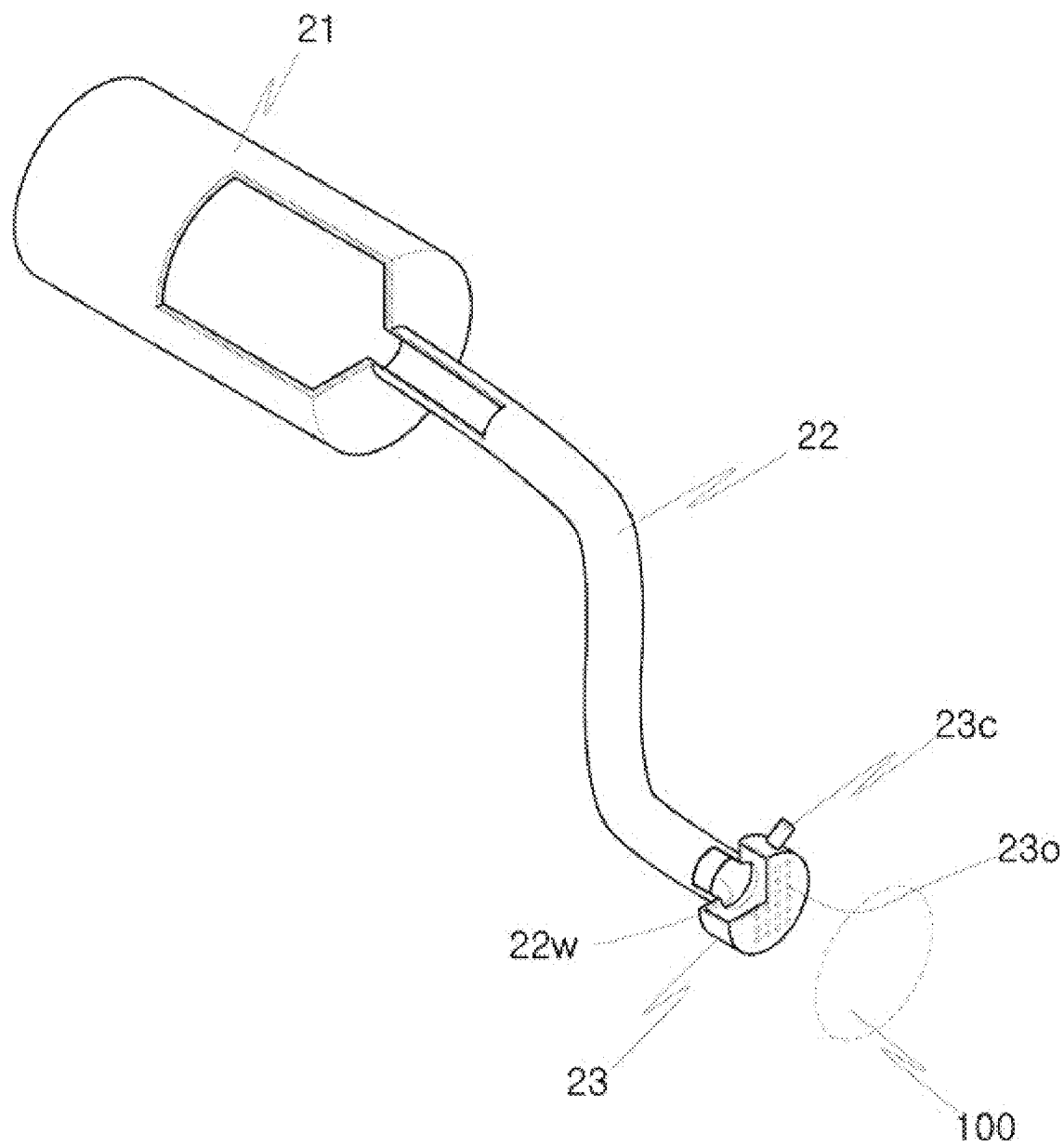
FIG. 2 is a perspective view of an apparatus for generating and transporting spectral line radiation according to another embodiment of the present invention.
Figure 3:
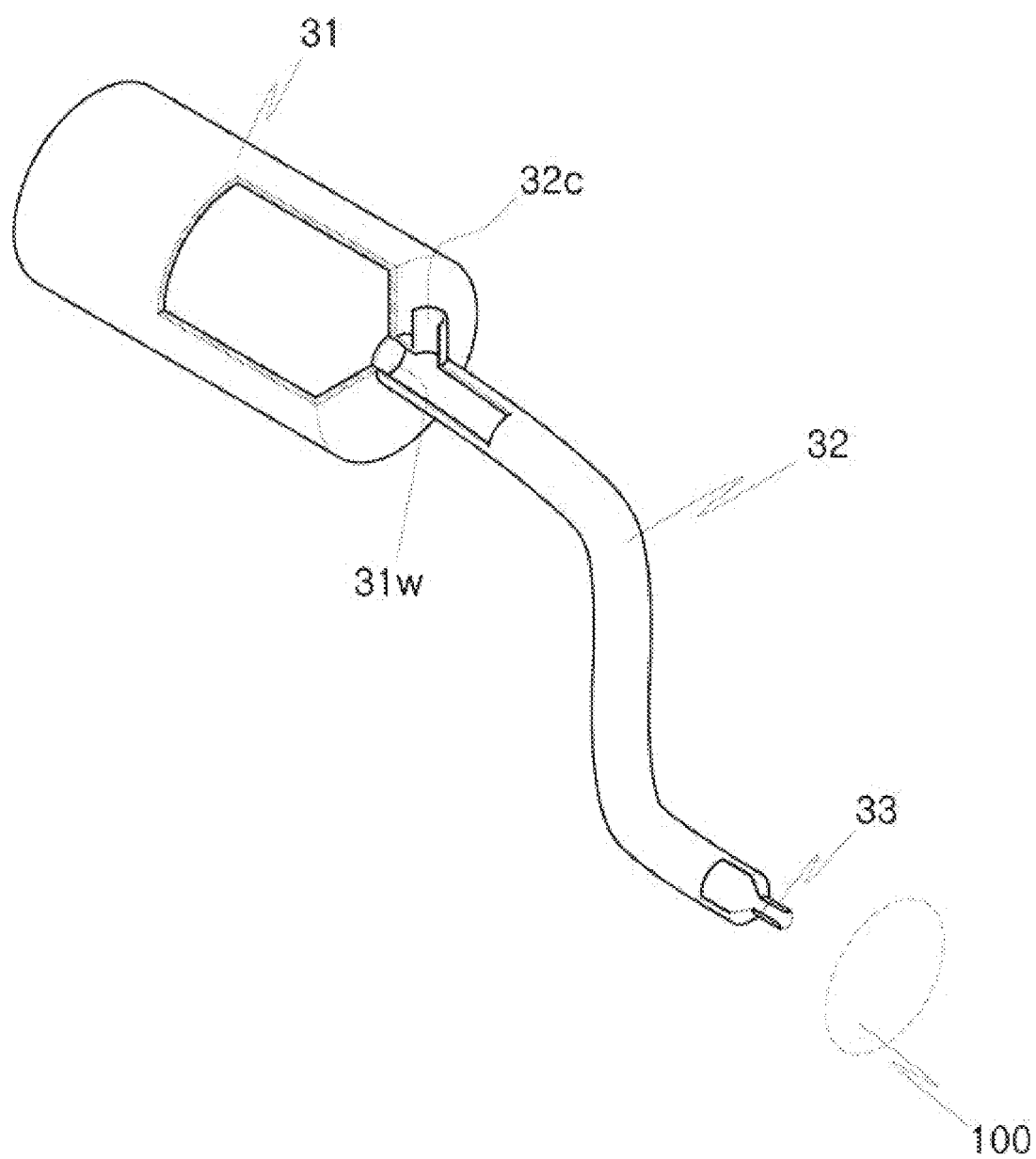
FIG. 3 is a perspective view of an apparatus for generating and transporting spectral line radiation according to still another embodiment of the present invention.
Figure 4:
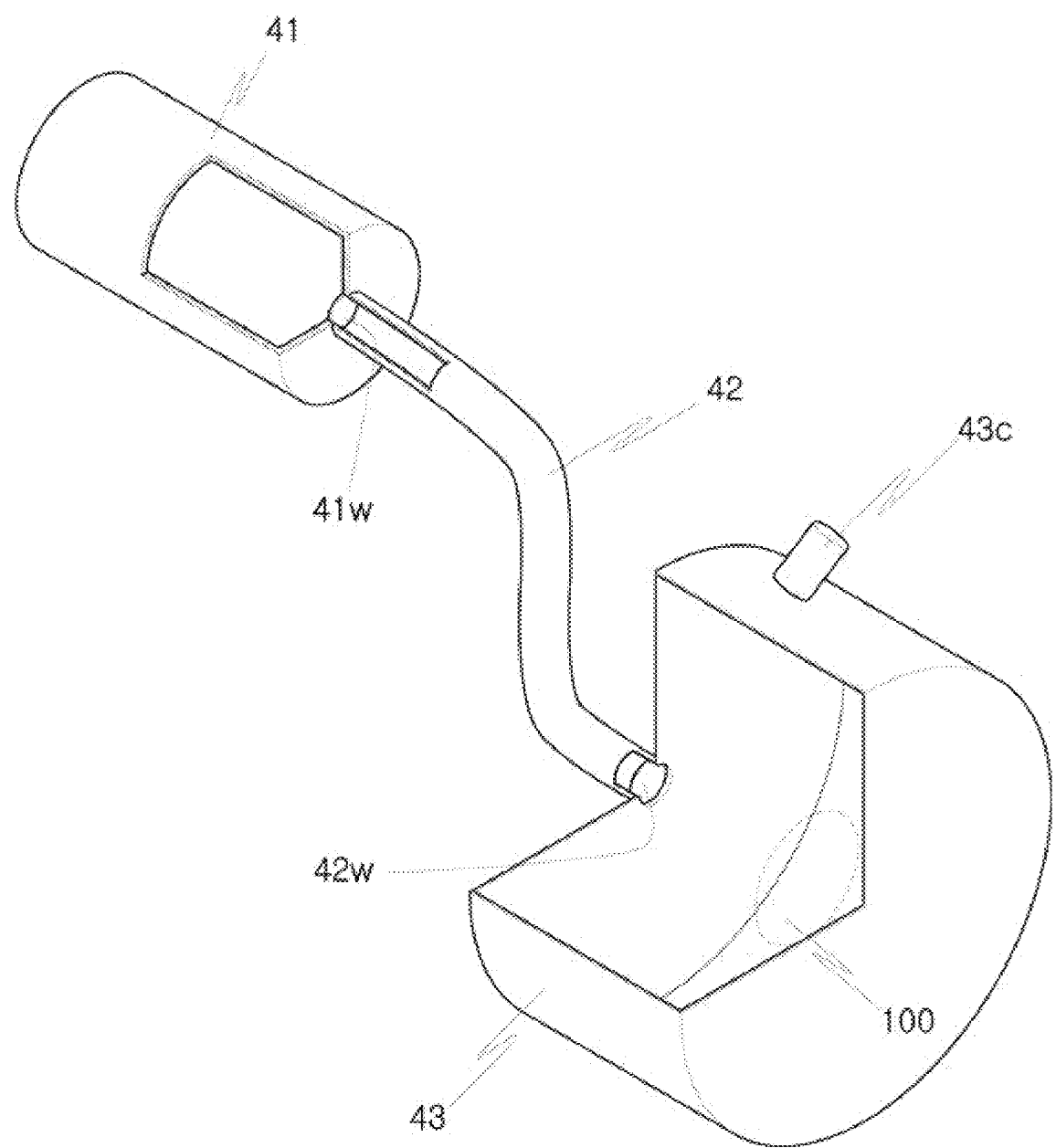
FIG. 4 is a perspective view of an apparatus for generating and transporting spectral line radiation according to yet another embodiment of the present invention.

The transmissive windows 11w, 31w, 41w or 61w and 12w, 22w or 42w are divided into a source transmissive window 11w, 31w, 41w or 61w installed at the outlet of the radiation source 11, 31, 41 or 61, as shown in FIGS. 1, 3, 4 and 6, and a conduit transmissive window 12w, 22w or 42w installed at the outlet of the transfer conduit 12, 22 or 42, as shown in FIGS. 1, 2 and 4, and, as needed, both the source transmissive window 11w, 31w, 41w or 61w and the conduit transmissive window 12w, 22w or 42w may be installed.

The transmissive windows 11w, 31w, 41w or 61w and 12w, 22w or 42w may be formed of one selected from the group consisting of group I-VII compounds and group II-VII compounds, or may be formed of one selected from the group consisting of group II-VI compounds, group III-V compounds, group IV-VI compounds and mixtures thereof.

The transmissive windows 11w, 31w, 41w or 61w and 12w, 22w or 42w may be formed of one of CaF, LiF, MgF, c-$Al_2O_3$, diamond and combinations thereof, or may be formed of one of other materials which transmit radial frequencies higher than the visible range of the electromagnetic spectrum or a wavelength range less than 300 nm.

The transmissive windows 11$w$, 31$w$, 41$w$ or 61$w$ and 12$w$, 22$w$ or 42$w$ may be formed of a transparent material having a thickness in the range of several nanometers to several millimeters.

Further, a reflective plate 11$r$ may be installed on the inner wall of the radiation source 11, 21, 31, 41, 51 or 61 (with reference to FIG. 1).

The reflective plate 11$r$ including a mirror having a planar shape or a geometric shape or a series of mirrors is additionally provided in a radiation source assembly, and thus reflects the spectral line radiation emitted by the radiation source 11, 21, 31, 41, 51 or 61 towards the transmissive window 11$w$, 31$w$, 41$w$ or 61$w$ and 12$w$, 22$w$ or 42$w$ and the transfer conduit 12, 22, 32, 42, 52 or 62.

The transfer conduit 12, 22, 32, 42, 52 or 62 serves as a path for transmitting the radiation emitted by the radiation source 11, 21, 31, 41, 51 or 61 to the transmission nozzle 13, 23, 33, 43, 53 or 63, and the transfer conduit 12, 22, 32, 42, 52 or 62 may have a length of several millimeters to several meters, as occasion demands, and may be rigid or flexible. The inner wall of the transfer conduit 12, 22, 32, 42, 52 or 62 may have high reflection characteristics at the wavelengths of the spectral line radiation emitted by the radiation source 11, 21, 31, 41, 51 or 61.

For this purpose, the transfer conduit 12, 22, 32, 42, 52 or 62 may be formed of a material having high reflection characteristics, or the inner wall of the transfer conduit 12, 22, 32, 42, 52 or 62 may be coated with a material having high reflection characteristics.

Figure 5:
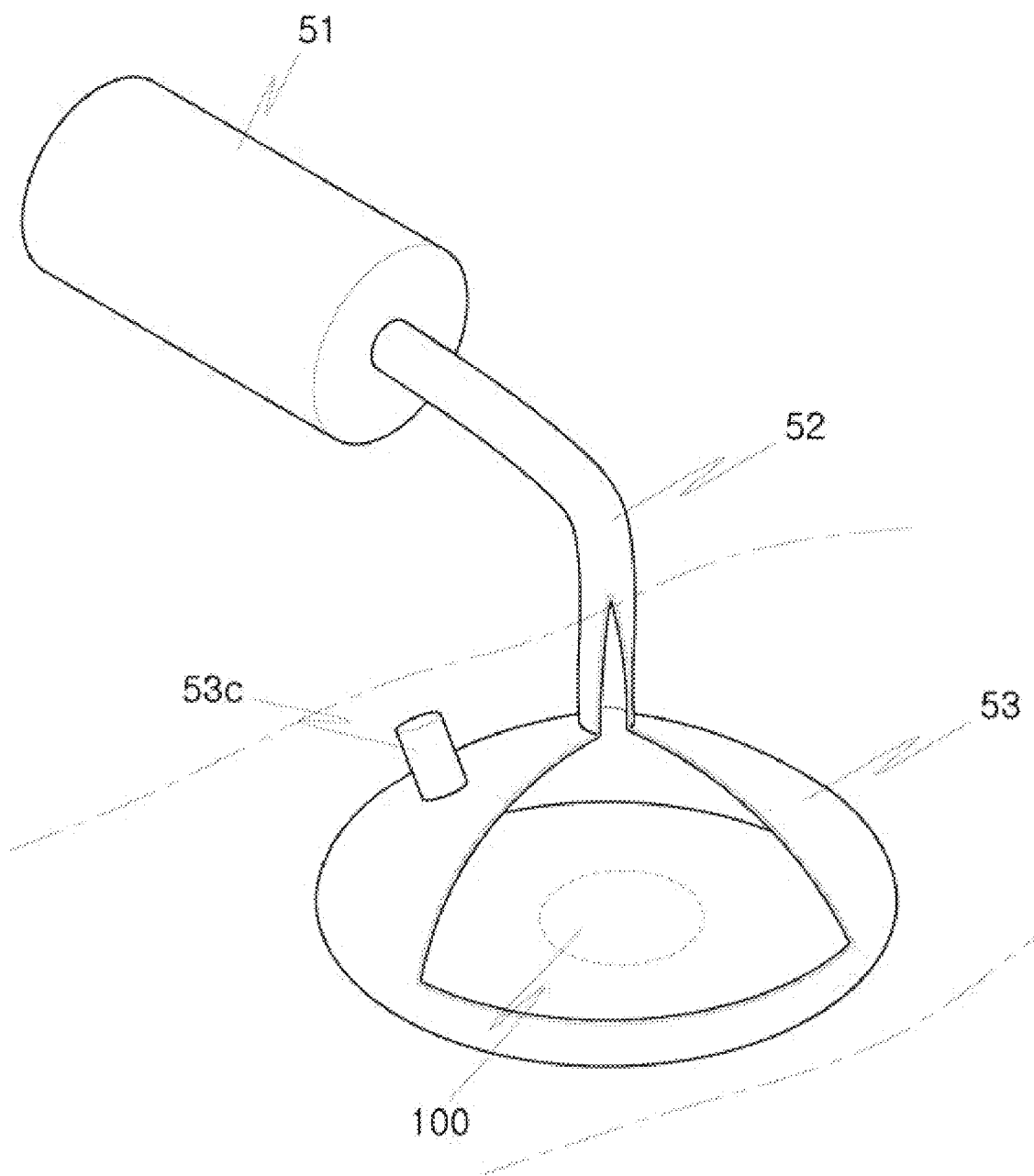
FIG. 5 is a perspective view of an apparatus for generating and transporting spectral line radiation according to still yet another embodiment of the present invention.

Among the transmission nozzles 13, 23, 33, 43, 53 and 63 according to the respective embodiments of the present invention, the transmission nozzle 33 according to one embodiment may be formed as an orifice, as shown in FIG. 3, the transmission nozzle 43 according to another embodiment may be formed as an enclosure, as shown in FIG. 4, and the transmission nozzle 53 according to yet another embodiment may be formed as a cup, as shown in FIG. 5.

Figure 6:
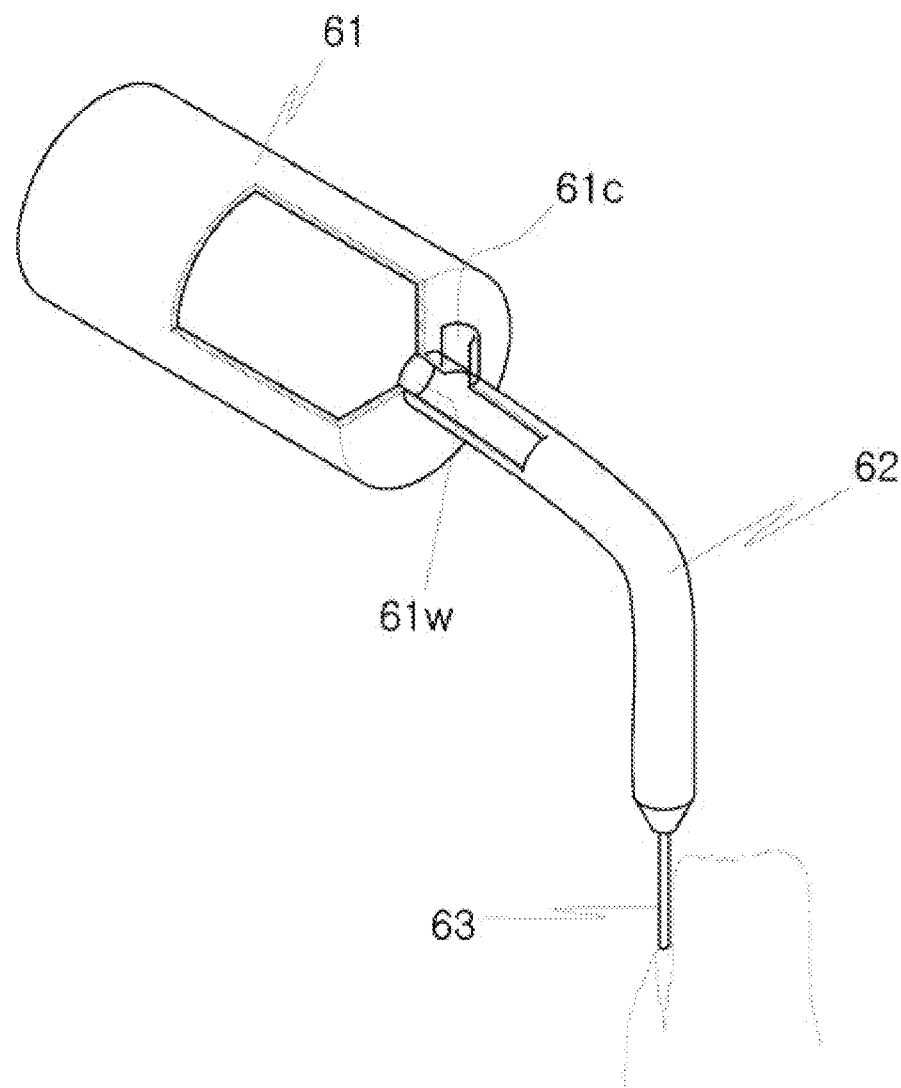
FIG. 6 is a perspective view of an apparatus for generating and transporting spectral line radiation according to a further embodiment of the present invention.

The gas supply channel 13$c$, 23$c$, 32$c$, 43$c$, 53$c$ or 62$c$ serves to supply gas to the inside of the transfer conduit 12, 22, 32, 42, 52 or 62 at a pressure in the range from high vacuum to atmospheric pressure, and may be formed at the transmission nozzle 13, 23, 43 or 53, as shown in FIGS. 1, 2, 4 and 5, or may be formed at the outlet of the radiation source 31 or 61, as shown in FIGS. 3 and 6.

Gas may include an element selected from the group consisting of molecules generated from mixtures of noble gas and other gases and excited mixtures of noble gas and other gases.

Hereinafter, the apparatus for generating and transporting spectral line radiation according to the present invention will be described in detail with reference to the accompanying drawings, the description will be made in order of the drawings, and a detailed description of some parts in the respective embodiments, which are substantially the same as those in other embodiments, will be omitted because it is considered to be unnecessary.

As described above, the apparatus for generating and transporting spectral line radiation according to the present invention basically includes the radiation source 11, 21, 31, 41, 51 or 61, the transfer conduit 12, 22, 32, 42, 52 or 62 and the transmission nozzle 13, 23, 33, 43, 53 or 63 or 53, and the radiation source 11, 21, 31, 41, 51 or 61, the transfer conduit 12, 22, 32, 42, 52 or 62 and the transmission nozzle 13, 23, 33, 43, 53 or 63 or 53 will be denoted by different reference numerals in consideration of partial structural differences thereamong and relations with other elements.

First, the radiation source 11 of the apparatus for generating and transporting spectral line radiation shown in FIG. 1 generates electromagnetic radiation having a narrow frequency distribution. That is, the radiation source 11 generates spectral line radiation, such as multiple frequencies generated by plasma or multiple frequencies generated by a laser.

Preferably, a plasma device may generate the high flux of spectral line radiation generated due to electronic transition in atoms, molecules and ions, and may have high energy conversion efficiency around a specific frequency or throughout a narrow frequency range. Plasma may be generated by applying a regular electric field to gas, such as direct current discharge.

More preferably, plasma may resonantly generate plasma discharge by applying an oscillating electric field to gas in the state in which there is a stable magnetic field configured to resonantly improve movement of electrons or ions in gas, such as helicon discharge, electron cyclotron resonant discharge, ion cyclotron resonant discharge or deformations thereof.

The transfer conduit 12 transfers the spectral line radiation generated by the radiation source 11 to the transmission nozzle 13.

The transfer conduit 12 is filled with gas having the same composition as in the radiation source 11 at atmospheric pressure, or more preferably, at a pressure equal to or less than atmospheric pressure.

The inner wall of the transfer conduit 12 may be coated with a reflective thin film so as to minimize loss due to the radiation.

Further, the transfer conduit 12 may be rigid, or more preferably, may be flexible.

The spectral line radiation flowing into the transfer conduit 12 is repeatedly absorbed and re-emitted by atoms, molecules or ions of the gas.

Such a process, known as radiation trapping, may transfer the spectral line radiation over a longer distance than allowed otherwise.

In spectral line radiation trapping, electronically excited atoms or ions emit spectral line radiation due to electron transition between an electronically excited state and a ground state.

When radiation meets atoms and ions having the same composition in the ground state, there is a high probability that the atoms or the ions absorb the radiation, and thus the atoms or the ions absorb the radiation and are converted into the electrically excited state. Then, the atoms or the ions may re-emit radiation at a different position, but do not necessarily emit the radiation in the direction of absorption of the radiation.

Therefore, in such a process, the spectral line radiation is moved towards an object having a shadow, and although the spectral line radiation was moved in one direction, the spectral line radiation is diffused three-dimensionally.

Due to such radiation diffusion, the transfer conduit 12 is bent in an arbitrary shape and has a very high aspect ratio.

When the density and temperature of gas in the transfer conduit 12 are appropriately selected, a probability of continuous absorption, re-emission and re-absorption of the radiation is higher than a probability of transmission of energy related to the spectral line to another electronic state of atoms or ions through competitive processes, such as leakage and loss of the radiation by the wall of the transfer conduit 12, or collision.

Alternatively, when the transfer conduit 12 has the wall which sufficiently reflects the frequencies of the spectral line radiation, the transfer conduit 12 may be sealed under high vacuum, and the above-described radiation trapping mechanism is not necessary in transmission of the spectrum line radiation In one embodiment, the radiation source 11 is separated from the transfer conduit 12 by the source transmissive window 11w configured to allow transmission of the spectral line radiation.

The source transmissive window 11w may be formed of one of CaF, LiF, MgF, c-$Al_2O_3$, diamond and combinations thereof, or one of other materials, and may transmit radial frequencies higher than the visible range of the electromagnetic spectrum (in general, a wavelength range less than 300 nm).

The surface of the source transmissive window 11w may be coated with a thin film so that radiation of a specific frequency range is selectively supplied from the radiation source 11 to the transfer conduit 12.

Further, the reflective plate 11r including a mirror having a planar shape or a geometric shape or a series of mirrors is selectively added to the radiation source assembly, and thus reflects the spectral line radiation emitted by the radiation source 11 towards the transmissive window 11w and the transfer conduit 12.

Further, the conduit transmissive window 12w having the same characteristics as the source transmissive window 11w may be further provided at the end of the transfer conduit 12.

The conduit transmissive window 12w serves to separate the transfer conduit 12 from the transmission nozzle 13 having a different pressure from the transfer conduit 12.

Gas in the radiation source 11 and the transfer conduit 12 travels towards the target 100 through the gas supply channel 13c and an outlet 13o.

Inside the transmission nozzle 13, the spectral line radiation transmitted by the source transmissive window 11w may be diffused as a result of the spectral line radiation trapping mechanism in which high spectral line radiation is injected into a region between the outlet 13o and the target 100, and in the frequency and short-wavelength (in general, less than 300 nm) radiation trapping mechanism, the spectral line radiation may be injected into a region around the target 100 and narrow spaces inside the target 100 including fine gaps, holes and pores.

The outlet 13o may include a single orifice, or a plurality of orifices so as to generate laminar flow and displace the surrounding environment around the target 100.

The above-described apparatus for generating and transporting spectral line radiation according to the present invention may be used to generate and transport energy spectral line radiation and to transmit the energy spectral line radiation to a target region at high efficiency.

The apparatuses for generating and transporting spectral line radiation according to other embodiments of the present invention include the three elements in the same manner as the above-described apparatus.

In another embodiment shown in FIG. 2, the radiation source 21 is directly coupled to the transfer conduit 22.

The radiation source 21 and the transfer conduit 22 are under the same conditions of pressure and gas composition.

The transmission nozzle 23 is connected to the transfer conduit 22, and is separated from the transfer conduit 22 by the conduit transmissive window 22w.

The transmission nozzle 23 is operated under the same conditions as the above-described transmission nozzle 13, and is provided with the gas supply channel 23c and an outlet 23o.

The apparatus shown in FIG. 2 is suitable for use of a spectral line radiation source operated in an excessively low pressure condition, such as magnetized resonant discharge plasma.

In still another embodiment shown in FIG. 3, the spectral line radiation source 31 is separated from the transfer conduit 32 by the source transmissive window 31w.

The gas supply channel 32c is formed at a part of the transfer conduit 32 connected to the radiation source 31.

Gas having the same composition as in the radiation source 31 is supplied through the gas supply channel 32c, and flows along the transfer conduit 32 towards the target 100 through the transmission nozzle 33.

The transmission nozzle 33 may be formed as an orifice, as shown in FIG. 3.

The apparatus for generating and transporting spectral line radiation according to yet another embodiment shown in FIG. 4 includes an enclosure 43 or a semi-enclosure provided at the end of the transfer conduit 42 so as to be filled with gas supplied through the gas supply channel 43c.

The target 100 is inserted into the enclosure 43, and is thus exposed to spectral line radiation diffused in the transfer conduit 42.

The enclosure 43 is filled with the gas supplied through the gas supply channel 43c, and may be at a pressure equal to or more than atmospheric pressure or at a pressure equal to or less than atmospheric pressure.

The spectral line radiation passing through the transfer conduit 42 is diffused into the enclosure 43 through the spectral line radiation trapping mechanism so as to be uniformly injected into the whole volume of the enclosure 43, thereby being capable of generating the uniform flux of the spectral line radiation in the enclosure 43.

The enclosure 43 or the semi-enclosure may include ports so that the target 100 may be inserted thereinto in a batch or consecutive processing mode.

As shown in FIG. 4, in the apparatus according to this embodiment of the present invention, a window may be provided or may not be provided between the radiation source 41 and the enclosure 43, the radiation source 41 may be directly mounted on the enclosure 43 without the transfer conduit 42, and such a configuration permits the highest flux of atomic spectral line radiation from a reactor towards the target 100, such as an object or an article, to be exposed.

The target 100, such as an object or an article, inside the enclosure 43 may be any object having an advantage in exposure of the surface of the object to high-frequency and short-wavelength spectral line radiation. That is, the target 100 may be an inorganic substance or an organic substance, or may be a biological object including a terminal of a human body or other body parts.

When a terminal of a human body is not capable of being directly inserted into the enclosure 43, a cup 53 shown in FIG. 5 may be used to isolate the terminal of the human body from the external surrounding environment.

In FIG. 5, the cup 53 is used to supply gas having the same type as gas used in the radiation source 51 to the target 100, exposed to the spectral line radiation emitted by the transfer conduit 52, and ambient air through positive pressure displacement or vacuum.

Atomic spectral line radiation generated by the radiation source 51 is diffused into the cup 53 so as to be supplied to the target 100, such as a part of a human body or other objects to be treated.

The gas supply channel 53c may be provided at one side of the cup 53.

Hereinafter, an applied example of the apparatus having the above-described configuration according to the present invention will be described.

As shown in FIG. 6, the apparatus according to the present invention may be used in dentistry, and may be used to transmit high-frequency or short-wavelength spectral lines to a target region.

In this embodiment, the apparatus includes the radiation source 61 separated from the transfer conduit 62 by the source transmissive window 61w.

Gas, which is the same as source gas used in the radiation source 61, flows into the transfer conduit 62 through the gas supply channel 62c formed at one side of the transfer conduit 62, is discharged to the outside through a lumen 63, and substitutes for ambient air and internal air due to positive displacement.

In this embodiment, the target 100, i.e., a target region, may be a region between teeth and gums of a human or mammal.

The spectral line radiation generated by the radiation source 61 is transmitted a region close to the target 100 through the transfer conduit 62 by the spectral line radiation transmission mechanism.

Interaction between the spectral line radiation and the exposed surface of the target 100 rapidly kills all bacteria exposed to the spectral line radiation, thereby exhibiting treatment and disinfection effects.

In order to prevent cross-contamination between patients, the lumen 63 is disposable so as to be replaceable, and may be separated from the transfer conduit 62.

The apparatus according to the present invention may be used to transmit spectral line radiation to the target 100, which is a target region, in the medical field, and the target region corresponding to the target 100 may be a part of a human or animal body through which a sharp object, such as a needle for injecting bodily fluid or a needle for removing bodily fluid, will pass.

In this embodiment, prior to injection into an body part, the body part is exposed to the radiation so that bacteria or other pathogens existing in gaps, holes or pores of the body part are killed so as to prevent bacteria or pathogens from entering the body part.

Figure 7:
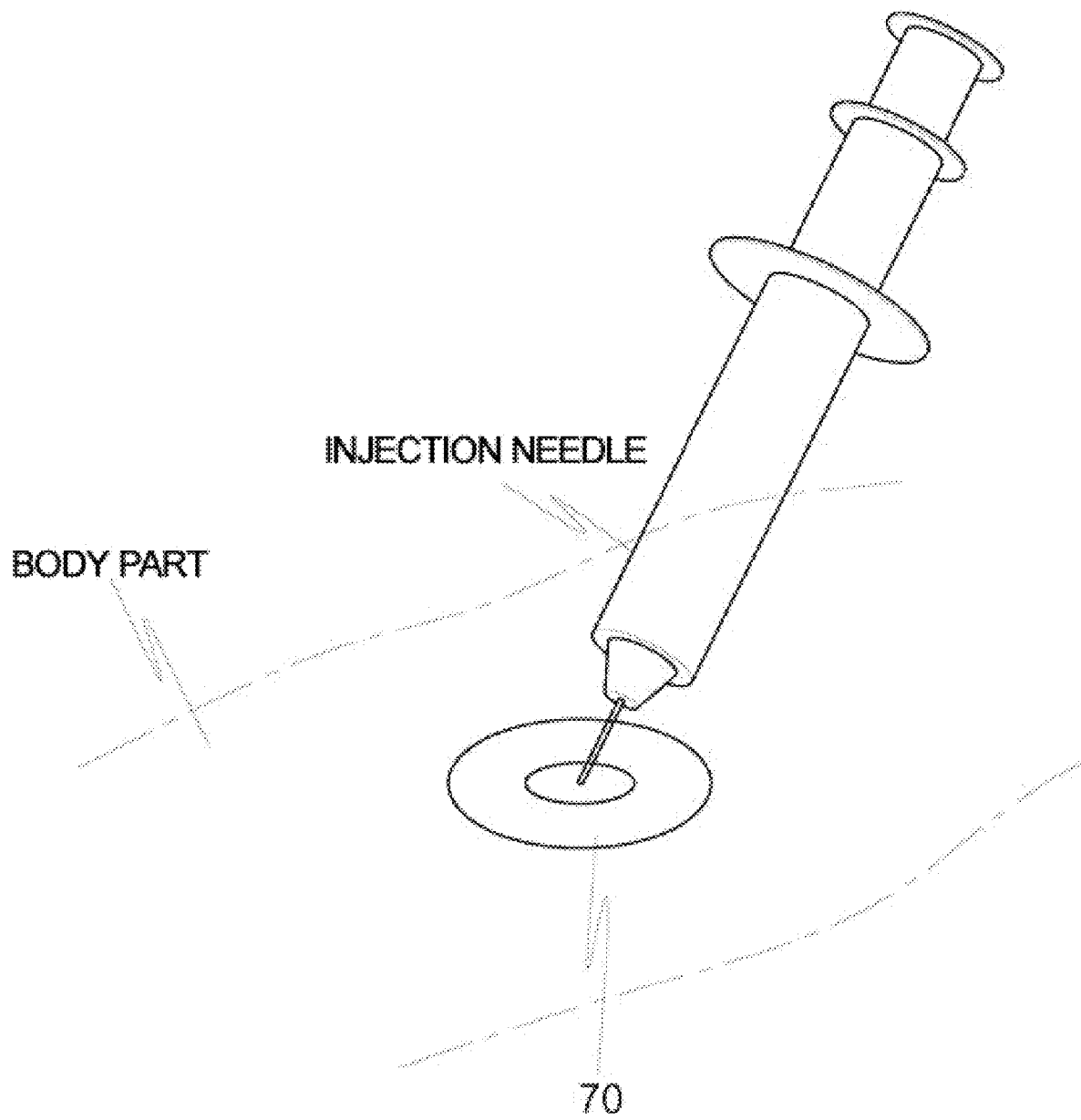
FIG. 7 is a perspective view illustrating a state in which an indicator is used in an apparatus for generating and transporting spectral line radiation according to the present invention.

In order to indicate the amount of radiation to which the body part is exposed prior to injection, a disposable indicator 70 may be used, as shown in FIG. 7.

Here, the indicator 70 may be designed to indicate a degree of exposure to spectral line radiation when the indicator 70 reacts to the radiation, and may be applied to the body part.

For example, the indicator 70 may include a compound designed to change the color thereof in proportion to the degree of exposure to spectral line radiation.

The indicator 70 may have a torus shape or other shapes suitable for the topology of a surface to be exposed.

In this embodiment, change in the color of the torus-type indicator 70 means exposure of a region inside a torus to a predetermined flux of the spectral line radiation.

After exposure, the cup 53 may be removed, a needle may be stuck into the region inside the torus, and thereby, inflow of live pathogens or bacteria into a body by the needle may be prevented.

After an operation has been completed, the indicator 70 may be removed from the body part and be destroyed or stored as a part of files or treatment records of a patient, and this preparation enables a site to be operated on to be sterilized to a predetermined level before tissues are punctured and may thus prevent nosocomial infection caused by inflow of pathogens on the surface of the body part into the body part.

The apparatus for generating and processing spectral line radiation according to the present invention may be used in semiconductor processing, and more particularly, may be used to transmit the high flux of the spectral line radiation to a surface in semiconductor processing.

The surface, to which the apparatus for generating and processing spectral line radiation according to the present invention is applied, may be the inner wall of a processing chamber or the surface of a wafer or a processing substrate, and this preparation using the apparatus may be used in pre-cleaning or cleaning, pre-deposition or post-deposition, pre-etching or post-etching, promotion of thin film adhesion, removal of organic residues, or change in chemical bonding of a thin film or other surfaces.

Due to isotropic characteristics of transmission of the spectral line radiation, the smallest surface including micrometer-sized or nanometer-sized structures of a substrate, such as channels or via holes, inside an enclosure may be exposed to the spectral line radiation regardless of the aspect ratio of a target.

As is apparent from the above description, an apparatus for generating and transporting spectral line radiation according to the present invention may transmit radiation generated from a radiation source accurately to a target.

Particularly, the apparatus according to the present invention may effectively transmit radiation having a narrow frequency range in a spectrum, which may be generated from various sources, such as gas discharge plasma or a laser, to an object (a target) to be exposed due to self absorption and re-emission of radiation.

Further, the apparatus according to the present invention re-distributes radiation directionally through radiation trapping, and may thus effectively transmit the radiation to a region above or behind the target or cracks, holes or via holes in the target when the radiation is buried in gas of the same type as gas used in generation of line radiation or when another source radiation exists.

Moreover, the apparatus according to the present invention enables an object to be effectively exposed narrow-band ultraviolet light or shorter-wavelength radiation, and may be used as an apparatus configured to kill bacteria on organisms and inorganic substances or an apparatus configured to change the chemical structure of a surface and a thin film used in semiconductor manufacture.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for generating and transporting spectral line radiation so as to apply the spectral line radiation to a target, the apparatus comprising:

a radiation source configured to emit atomic, ionic or molecular spectral line radiation, wherein the spectral line radiation includes electromagnetic radiation having a narrow frequency distribution and is generated by atomic, ionic, or molecular electronic transitions;

a transmission nozzle configured to transmit the spectral line radiation emitted by the radiation source to the target; and a gas supply channel configured to supply gas in a same environment as the spectral line radiation emitted by the radiation source to an environment around the target.

2. The apparatus according to claim 1, further comprising a transfer conduit configured to transmit the spectral line radiation emitted by the radiation source to the transmission nozzle.

3. The apparatus according to claim 1, wherein the radiation source is any one of a plasma device, a laser device and a light emitting diode.

4. The apparatus according to claim 1, wherein a transmissive window is further installed in at least one of the radiation source and the transfer conduit.

5. The apparatus according to claim 4, wherein a reflective plate is further installed on an inner wall of the radiation source.

6. The apparatus according to claim 5, wherein an inner wall of the transfer conduit has high reflection characteristics at wavelengths of the spectral line radiation emitted by the radiation source.

7. The apparatus according to claim 1, wherein the transmission nozzle is an enclosure.

8. The apparatus according to claim 1, wherein the transmission nozzle is an orifice.

9. The apparatus according to claim 1, wherein the transmission nozzle is a cup.

10. The apparatus according to claim 1, wherein an indicator is further provided at one side of the apparatus.

* * * * *